(12) United States Patent
Speier et al.

(10) Patent No.: US 6,531,869 B1
(45) Date of Patent: Mar. 11, 2003

(54) METHODS AND APPARATUS FOR MEASURING FLOW VELOCITY IN A WELLBORE USING NMR AND APPLICATIONS USING SAME

(75) Inventors: Peter Speier, Stafford, TX (US); Julian Pop, Houston, TX (US); Martin Poitzsch, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 10/242,592

(22) Filed: Sep. 12, 2002

Related U.S. Application Data

(62) Division of application No. 09/951,914, filed on Sep. 10, 2001.

(51) Int. Cl.[7] .............................................. G01V 3/00
(52) U.S. Cl. ...................................... 324/303; 324/306
(58) Field of Search ................................ 324/303, 306, 324/307, 309, 312, 314, 318, 300

(56) References Cited

U.S. PATENT DOCUMENTS

| | | | |
|---|---|---|---|
| 5,212,447 A | * 5/1993 | Paltiel | ......................... 324/300 |
| 5,428,291 A | * 6/1995 | Thomann et al. | ............ 324/303 |
| 5,698,979 A | * 12/1997 | Taicher et al. | ............... 324/303 |
| 5,796,252 A | * 8/1998 | Kleinberg et al. | ........... 324/303 |

* cited by examiner

*Primary Examiner*—Louis Arana
(74) *Attorney, Agent, or Firm*—Kevin P. McEnaney; Brigitte L. Jeffery

(57) ABSTRACT

The present invention provides methods and apparatus for determining flow velocity within a formation utilizing nuclear magnetic resonance (NMR) techniques in which the shape of the resonance region is restricted so that sensitivity to radial flow or vertical flow is obtained (or both when more than one NMR tool is used). Flow velocity using these NMR tools is determined using decay amplitude, frequency displacement or stimulated echoes (where the spins are stored along the magnetic field instead of the transverse plane to exploit echo decays and frequency displacements) based on the application of adiabatic pulses. Based on the described NMR measurement of flow velocity, additional wellbore parameters may be obtained such as a direct measurement of permeability, an assessment of drilling damage to the wellbore, formation pressure, invasion rate of the mud filtrate or the migration of fine mud particles during sampling operations.

16 Claims, 5 Drawing Sheets

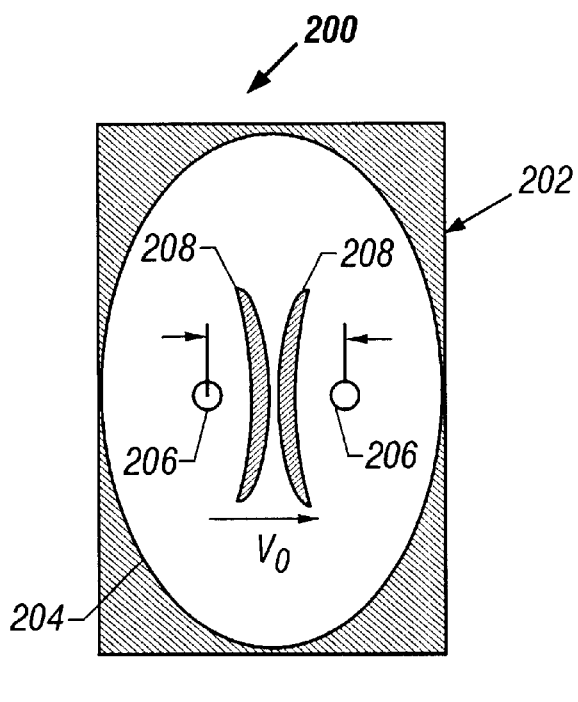
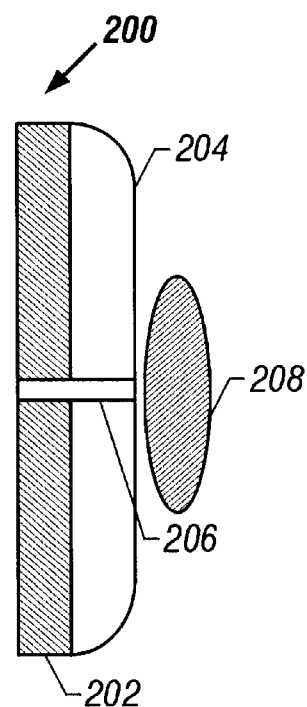
FIG. 2A  FIG. 2B
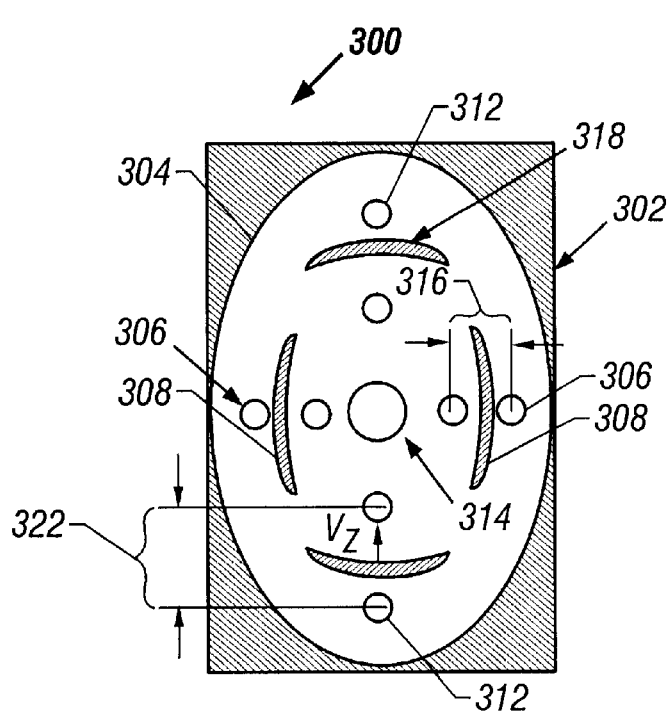
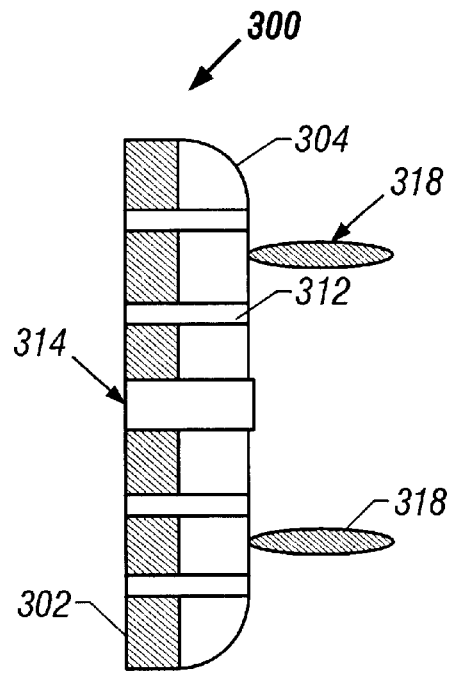
FIG. 3A  FIG. 3B

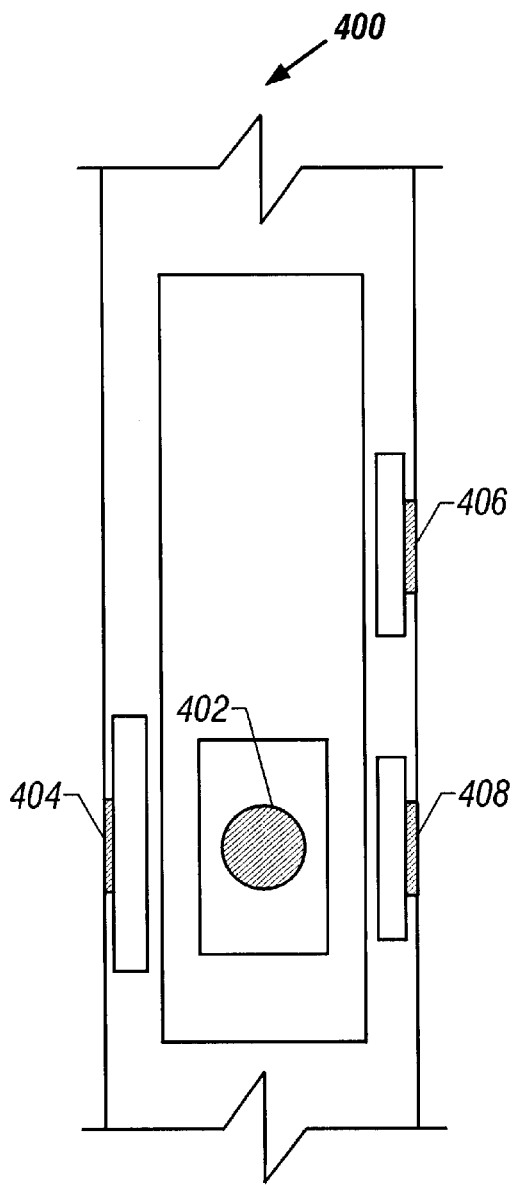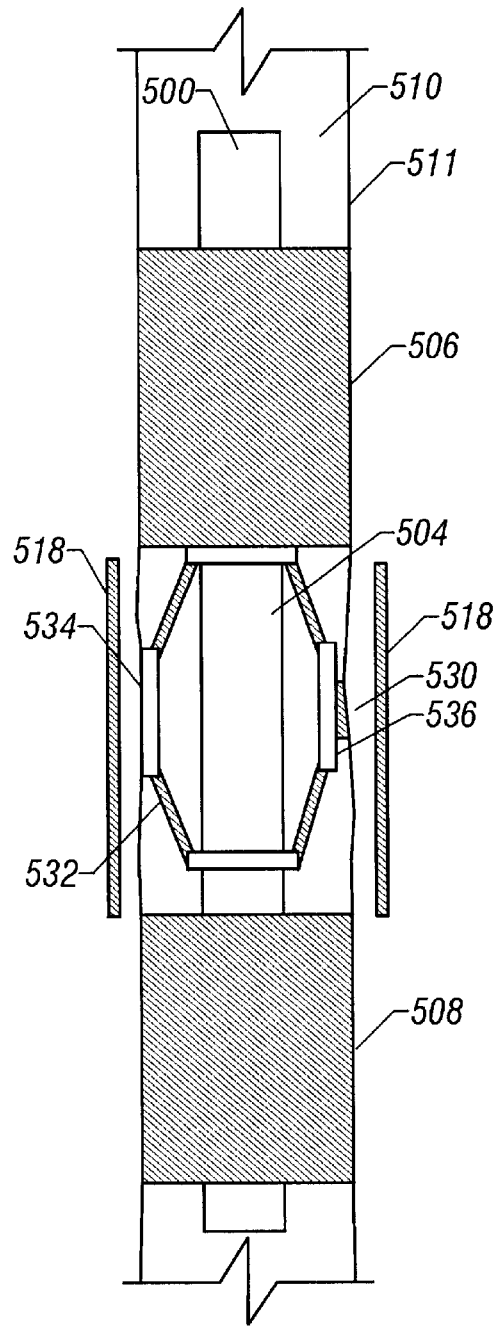
FIG. 4
FIG. 5

METHODS AND APPARATUS FOR MEASURING FLOW VELOCITY IN A WELLBORE USING NMR AND APPLICATIONS USING SAME

This is a division of U.S. patent application Ser. No. 09/951,914, filed Sep. 10, 2001.

FIELD OF THE INVENTION

This invention relates to the field of well logging of earth wellbores and, more particularly, to methods for measuring flow velocity in an earth formation with nuclear magnetic resonance techniques and for using the measured flow velocity to determine various other important well logging parameters.

BACKGROUND OF THE INVENTION

Well logging provides various parameters that may be used to determine the "quality" of a formation from a given wellbore. These parameters include such factors as: formation pressure, resistivity, porosity, bound fluid volume and hydraulic permeability. These parameters, which are used to evaluate the quality of a given formation, may provide, for example, the amount of hydrocarbons present within the formation, as well as an indication as to the difficulty in extracting those hydrocarbons from the formation. Hydraulic permeability—how easily the hydrocarbons will flow through the pores of the formation—is therefore, an important factor in determining whether a specific well site is commercially viable.

There are various known techniques for determining hydraulic permeability, as well as other well logging parameters. For example, it is known how to derive permeability from nuclear magnetic resonance (NMR) measurements. NMR measurements, in general, are accomplished by causing the magnetic moments of nuclei in a formation to precess about an axis. The axis about which the nuclei precess may be established by applying a strong, polarizing, static magnetic field ($B_0$) to the formation, such as through the use of permanent magnets (i.e., polarization). This field causes the proton spins to align in a direction parallel to the applied field (this step, which is sometimes referred to as longitudinal magnetization, results in the nuclei being "polarized"). Polarization does not occur immediately, but instead grows in accordance with a time constant $T_1$, as described more fully below, and may take as long as several seconds to occur (even up to about eight seconds or longer). After sufficient time, a thermal equilibrium polarization parallel to $B_0$ has been established.

Next, a series of radio frequency (RF) pulses are produced so that an oscillating magnetic field $B_1$, is applied. The first RF pulse (referred to as the 90° pulse) must be strong enough to rotate the magnetization from $B_0$ substantially into the transverse plane (i.e., transverse magnetization). The rotation angle is given by:

$$\alpha = B_1 \gamma t_p \quad (1)$$

and is adjusted, by methods known to those skilled in the art, to be 90° (where $t_p$ is the pulse length and $\gamma$ is the gyromagnetic ratio—a nuclear constant). Additional RF pulses (referred to as 180° pulses where $\alpha=180°$) are applied to create a series of spin echoes. The additional RF pulses typically are applied in accordance with a pulse sequence, such as the error-correcting CPMG (Carr-Purcell-Meiboom-Gill) NMR pulse sequence, to facilitate rapid and accurate data collection. The frequency of the RF pulses is chosen to excite specific nuclear spins in the particular region of the sample that is being investigated. The rotation angles of the RF pulses are adjusted to be 90° and 180° in the center of this region.

Two time constants are associated with the relaxation process of the longitudinal and transverse magnetization. These time constants characterize the rate of return to thermal equilibrium of the magnetization components following the application of each 90° pulse. The spin-lattice relaxation time ($T_1$) is the time constant for the longitudinal magnetization component to return to its thermal equilibrium (after the application of the static magnetic field). The spin-spin relaxation time ($T_2$) is the time constant for the transverse magnetization to return to its thermal equilibrium value which is zero. Typically, $T_2$ distributions are measured using a pulse sequence such as the CMPG pulse sequence described above. In addition, $B_0$ is typically inhomogeneous and the transverse magnetization decays with the shorter time constant $T_2^*$, where:

$$\frac{1}{T_2^*} = \frac{1}{T_2} + \frac{1}{T'} \quad (2)$$

In the absence of motion and diffusion, the decay with characteristic time T' is due to $B_0$ inhomogeneities alone. In this case, it is completely reversible and can be recovered in successive echoes. The amplitudes of successive echoes decay with $T_2$. Upon obtaining the $T_2$ distributions, other formation characteristics, such as permeability, may be determined.

A potential problem with the $T_2$ distributions may occur if the echo decays faster than predicted, for example, if motion of the measuring probe occurs during measurements. Under these conditions, the resultant data may be degraded. Thus, for example, displacement of the measurement device due to fast logging speed, rough wellbore conditions or vibrations of the drill string during logging-while-drilling (LWD) may prevent accurate measurements from being obtained.

Moreover, it also is known that $T_2$ distributions do not always accurately represent pore size. For example, G. R. Coates et al., "A New Characterization of Bulk-Volume Irreducible Using Magnetic Resonance," SPWLA 38th Annual Logging Symposium, Jun. 15–18, 1997, describes the measurement of bound fluid volume by relating each relaxation time to a specific fraction of capillary bound water. This method assumes that each pore size has an inherent irreducible water saturation (i.e., regardless of pore size, some water will always be trapped within the pores). In addition, the presence of hydrocarbons in water wet rocks changes the correlation between the $T_2$ distribution and pore size.

Hydraulic permeability of the formation is one of the most important characteristics of a hydrocarbon reservoir and one of the most difficult quantitative measurements to obtain. Often permeability is derived from $T_2$ distributions, created from NMR experiments, which represent pore size distributions. Finally, permeability is related to the $T_2$ data. This way to determine permeability has several drawbacks and is therefore sometimes inapplicable.

Typically $T_2$ distributions are measured using the error-correcting CPMG pulse sequence. In order to provide meaningful results, the length of the recorded echo train must be at least $T_2^{max}$. During this time period, as well as during the preceding prepolarization period, the measurement is sensitive to displacements of the measuring device. Further, in some cases, the $T_2$ distributions do not represent pore size distributions, e.g., hydrocarbons in water wet rocks change the correlation between $T_2$ distribution and pore size distribution. Finally, the correlation between pore size distribution and permeability of the formation is achieved using several phenomenological formulae that are based on large measured data sets, displaying relatively weak correlation. In carbonates, these formulae breakdown because of the formations' complex pore shapes.

A more direct way to measure permeability is by measurements of induced flow rates using a packer or probe tool. Still, this measurement requires extensive modeling of the formation response which includes the geometry of the reservoir and of the tool, the mud cake, and the invasion zone. The effort required for modeling however, could be significantly reduced if flow velocity could be obtained. It would be advantageous to obtain flow velocity, which could be used to determine various parameters required for modeling so that the number of variables required for modeling is reduced.

For at least the foregoing reasons, it is an object of the present invention to provide apparatus and methods for determining flow velocity utilizing NMR techniques.

It is a still further object of the present invention to provide methods for determining permeability utilizing NMR measurements of flow velocity.

It is an even further object of the present invention to provide methods for determining the extent of drilling damage to the formation, formation pressure, mud filtration rate and changes in the invaded zone during sampling utilizing NMR measurements of flow velocity.

SUMMARY OF THE INVENTION

These and other objects of the invention are accomplished in accordance with the principles of the invention by providing methods and apparatus for determining flow velocity utilizing nuclear magnetic resonance (NMR) techniques and for providing measurements of other wellbore parameters based on the flow velocity measurements. The preferred embodiments include methods and apparatus in which flow velocity is determined without knowledge of $T_2$ or the pressure distribution. The flow velocity measurements are made using NMR techniques in which the shape of the resonance region is varied depending on whether radial or vertical sensitivity is desired. In an embodiment that requires knowledge of $T_2$, the decay of the echo amplitude is measured. If both radial and vertical sensitivity are desired, multiple NMR devices may be provided in a single wellbore tool where each NMR device is designed to measure a specific orientation.

In other preferred embodiments of the present invention, NMR determination of frequency displacement, rather than signal decay, is utilized to determine flow velocity. An advantage of these techniques also is that no reference measurements need be taken because the detection of signal decay is not employed. This can be achieved by analyzing the echo shape instead of the echo amplitude or by standard NMR one-dimensional frequency selective or two-dimensional methods. In still other preferred embodiments, an encoding pulse is substituted for the traditional 90° pulse, and adiabatic pulses are substituted for the traditional 180° pulses. These techniques are advantageous if the $B_0$ gradient is small, e.g., in the case of a $B_0$ saddle point, because only an inhomogeneous field $B_1$ is required, rather than a $B_0$ gradient.

The methods and apparatus of the present invention for obtaining flow velocity using NMR techniques also are applicable to determining various wellbore parameters during wellbore drilling operations. For example, by inducing fluid to flow within the formation such as by withdrawing fluid from the formation into the NMR tool or into the wellbore, the NMR determination of flow velocity may be used in conjunction with a differential pressure measurement to provide a direct, small-scale measurement of permeability due to the fact that the NMR data provides an extremely localized measurement of fluid velocity. Alternatively, the NMR techniques of the present invention may be used to obtain an assessment of the drilling damage to the formation.

In addition, the NMR techniques of the present invention may be used to determine formation pressure by establishing conditions in the wellbore (for example, by using a packer module) such that no filtration of wellbore fluid occurs across the mudcake and simultaneously measuring the pressure at the interface between the mudcake and the formation. Another important parameter that may be determined using the NMR techniques of the present invention is mud filtration rate (sometimes referred to as invasion). This parameter may be particularly important because it provides a direct measure of the quality of the mud system being employed and may provide an advance indication of potential problems. Also, the NMR techniques of the present invention may be used to monitor changes in the invaded zone during sampling operations. Under such conditions, it is often important to monitor the migration of fine mud particles (or "fines") that may give rise to plugging of the formation where the sampling is being conducted. Moreover, while the determination of various operational parameters is described herein, persons skilled in the art will appreciate that various other parameters may be obtained utilizing the NMR techniques of the present invention.

BRIEF DESCRIPTION OF THE DRAWINGS

FIG. 2a is a plan-view schematic representation of one embodiment of an NMR tool component that may be utilized in conjunction with the NMR logging apparatus of FIG. 1 in accordance with the principles of the present invention;

FIG. 2b is a cross-sectional-view schematic representation of one embodiment of an NMR tool component that may be utilized in conjunction with the NMR logging apparatus of FIG. 1 in accordance with the principles of the present invention;

FIG. 3a is a plan-view schematic representation of another embodiment of an NMR tool component that may be utilized in conjunction with the NMR logging apparatus of FIG. 1 in accordance with the principles of the present invention;

FIG. 3b is a cross-sectional-view schematic representation of another embodiment of an NMR tool component that may be utilized in conjunction with the NMR logging apparatus of FIG. 1 in accordance with the principles of the present invention;

FIG. 4 is a side-view schematic representation of one embodiment of a pressure measurement tool component that may be used in conjunction with the NMR tool components of FIGS. 2 and 3 in accordance with the principles of the present invention;

FIG. 5 is a schematic diagram of another embodiment of an NMR logging apparatus in accordance with the principles of the present invention;

DETAILED DESCRIPTION OF THE PREFERRED EMBODIMENTS

The methods and apparatus of the present invention utilize several techniques to determine various qualitative parameters regarding a given formation from NMR measurements. The initial techniques provide a measurement of formation fluid speed (i.e., flow velocity) that leads to a determination of formation pressure and/or mud filtration rate. To accomplish these techniques, the NMR tool must include the ability to induce flow in the formation (one tool component) and to create an NMR shell in the formation that is used to measure the induced flow (a second tool component). When the basic techniques described herein are supplemented by measurements of local pressure gradient (e.g., by adding a third tool component to the drill string), the techniques of the present invention may also provide a determination of permeability and/or skin damage (i.e., the area between the wellbore and the virgin formation).

Described herein are various ways to induce fluid to flow within the wellbore in conjunction with the determination of flow velocity. For example, during drilling, the pressure in the wellbore fluid may be changed via an external device such as a rig pump. Alternatively, a tool such as that shown in FIG. 1 and described below may be deployed (drilling would not be occurring under these circumstances) that pumps fluid into or withdraws it from the packer interval. Still another way to induce fluid flow is through the use of a port located on a pad, such as that shown in FIGS. 3a and 3b and described below, in which case fluid would again be pumped into or out of the tool.

Various known techniques exist for determining flow velocity. For example, NMR techniques may utilize switched gradients to encode flow and diffusion. However, under certain circumstances switched gradients may be difficult, if not impossible, to produce, and in the presence of large static gradients, they may be negligible. The echo measurements of the present invention can be produced such that they rely only on static gradient $B_0$ or $B_1$ fields instead of switched gradients, and therefore, it works for "inside out" NMR conditions where measurements are made outside the magnet configuration.

Figure 1:
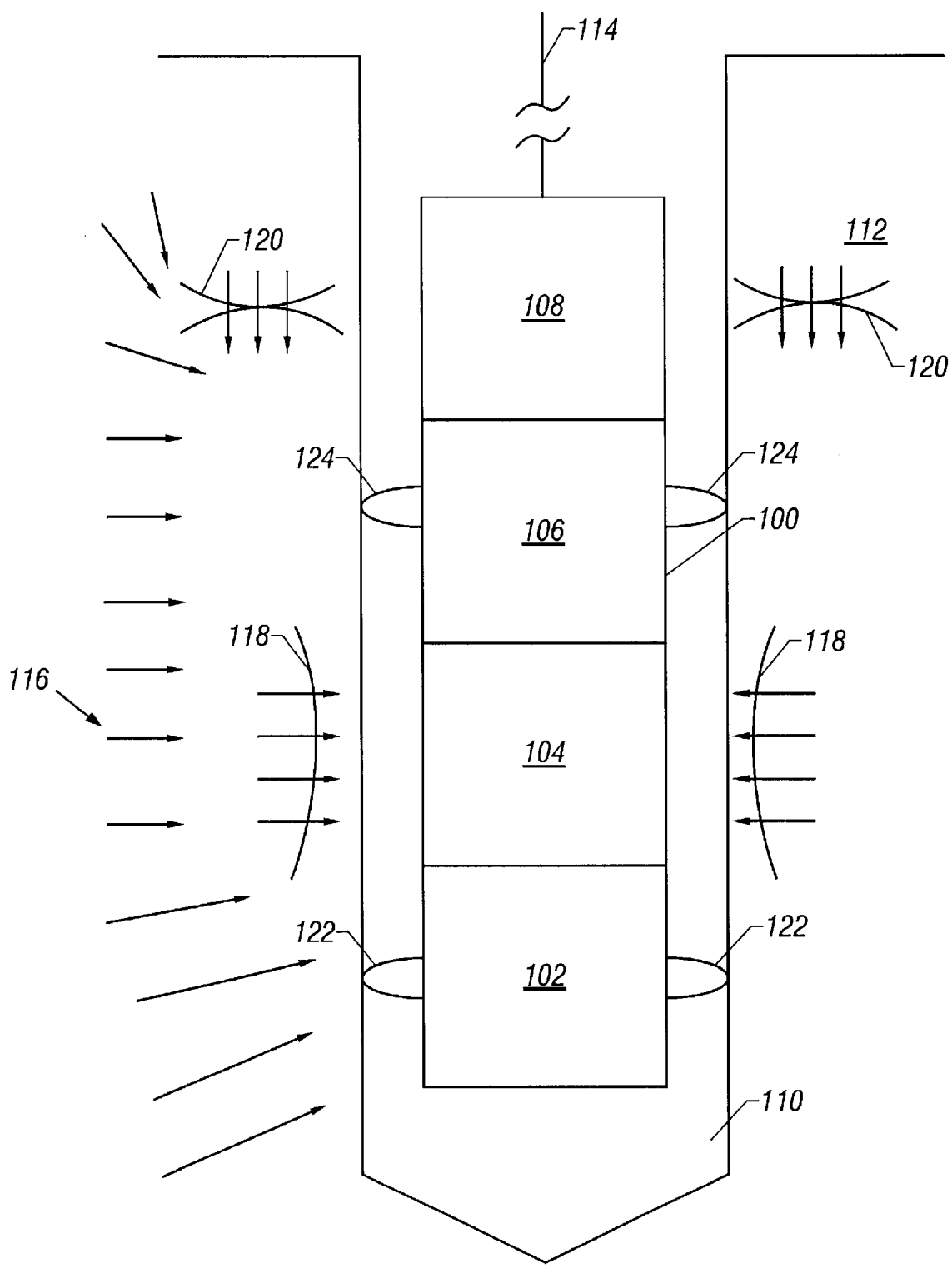
FIG. 1 is a schematic diagram of one embodiment of an NMR logging apparatus for measuring flow velocity in accordance with the principles of the present invention.

FIG. 1 shows an illustrative example of an NMR logging device 100 that measures flow velocity. Logging device 100 includes four modules including: packer 102, NMR tool 104, packer 106 and NMR tool 108. While logging device 100 is shown having four modules, persons skilled in the art will appreciate that various other combinations of logging tools may be used, including other known logging tools that are not mentioned herein. For example, logging device 100 may be used without NMR tool 108, in which case device 100 only would have three modules.

As shown in FIG. 1, logging device 100 is located in wellbore 110 that previously has been drilled in earth formation 112. Logging device 100 is suspended in wellbore 110 from logging cable 114. It is within contemplation of this invention for the logging device 100 to be conveyed in the wellbore by drill pipe or coiled tubing. As described in more detail below, the principles of the present invention also may be applied to logging-while-drilling (LWD) operations, in which case logging device 100 (or the applicable modules (e.g., packers)) then would be located within a drill string (not shown) behind the drill bit (not shown). Also shown in FIG. 1 are flow lines 116, and resonance lines 118 and 120 that are explained in more detail below.

It is known that a net displacement of a resonated substance with respect to its spatial position in the field maps of the measuring device at the moment of excitation by a pulse sequence leads to a decreased decay amplitude (DA) in the measured signal amplitude A. This displacement may be a product of actual displacement, translational diffusion or a combination of both. Normal NMR multi-echo experiments correct to a high degree for diffusion, so that given sufficiently short echo spacing only the total displacement due to diffusion at detection time is important. Directed flow, however, can be detected even in the presence of diffusion as long as the displacement due to flow is at least comparable to the displacement due to diffusion.

The loss of the I-th echo can be characterized by a loss factor: $\lambda_i = A_i/A^0_i$, where $A^0_i$ is the amplitude of the I-th echo under the same circumstances except for no displacement. Importantly, the loss factor is independent of the relaxation time distribution of the substance being investigated, if the displacement is caused by a uniform motion with a constant scalar velocity v, the loss factor vector is a function of v only (i.e., a single variable). Therefore, velocity v may be determined from the loss factor vector $\lambda^\wedge$ (vectors herein are denoted with the character "^") This requires that several measurements be made with varying velocities. Let the measured response vector be $S_V^\wedge = \{A_1, \ldots, A_n\}$ and assume a measured response, such as for v=0, produces a response vector $S_0^\wedge = \{A^0_1, \ldots, A^0_n\}$, then the characteristic loss factor vector is directly given by $\lambda^\wedge = \{A_1/A^0_1, \ldots, A_n/A^0_n\}$. Thus, for a given measurement apparatus with known field maps and a fixed pulse sequence, a lookup table of $\lambda^\wedge(v)$ can be calculated from which v can be derived.

The methods and apparatus of the present invention utilize an excitation pulse in accordance with field maps $B_0$ and $B_1$ that cause the resonance region where spins are excited by the pulse to have a specific shape. The specific shapes are selected depending on the general direction of fluid flow that is being measured. For example, if radial flow is an important component of a desired measurement, the NMR tool used in flow velocity measurement is configured such that a thin, long, cylindrically-shaped resonance region is defined. A cylindrically-shaped resonance region is essentially unaffected by vertical displacements (such as, for example, vertical movement of logging drill string 114), while being especially sensitive to radial movement. It can be created, for example, using an axisymmetric gradient design for $B_0$ like that employed in the MRIL® tool of the Numar Corporation.

On the other hand, if vertical displacement is an important factor, the NMR tool may be configured to provide a resonance region that is essentially a flattened torus-shape (like a flattened doughnut). A flattened torus-shaped resonance region, which is especially sensitive to vertical displacement, may be created, for example, by using a Jasper-Jackson saddle point design and tuning the operating frequencies above the Larmor frequency at the saddle point (see U.S. Pat. No. 4,350,955). When both radial and vertical displacement are important parameters, two separate NMR tools, such as tools 104 and 108 of FIG. 1, may be utilized. Under such circumstances, NMR tool 104 may be configured to form a cylindrically-shaped resonance region, while NMR tool 108 may be configured to form a flattened torus-shaped resonance region. Additionally, if a gradient $B_1$ field is present, it is also possible to utilize a saddle-point-shaped $B_0$ at resonance.

In addition to determining flow velocity v from the loss factor $\lambda_i$, it is also possible to determine flow velocity by analyzing the echo shape in either the frequency or time domain. Or, the fact that flow causes the phases of the echoes to shift in the x-y plane (of the conventional NMR "rotating" coordinate system) can be utilized to characterize the motion and further enhance resolution. The correction vector $\lambda^{\wedge}(v)$, thus can be determined solely by quantitative analysis of the recorded echo phases and echo shapes in the time domain or frequency domain and knowledge of the $T_2$ distribution is not required. In the case of a monotonic gradient G, it is possible to obtain information about the flow direction by qualitative analysis of the echo shape.

As described above, FIG. 1 shows one embodiment of an NMR logging device 100 that includes two NMR tools 104 and 108, each being configured to measure a different aspect of flow velocity. As NMR tool 104 is configured to measure radial displacement, its resonance region is illustrated by resonance lines 118, while resonance lines 120 illustrate the vertically oriented resonance region of NMR tool 108 (note that flow lines 116 pass through resonance lines 118 and 120). In addition, packers may be used to create a specific flow path. For example, FIG. 1 shows NMR tool 104 between packers 102 and 106 in an isolated portion of wellbore 110. Packers 102 and 106 utilize expansion components 122 and 124, respectively, to effectively seal off a portion of the wellbore. Then, NMR tool 104 induces fluid flow by drawing fluid from the wellbore into the tool itself through a fluid inlet port. This creates a local pressure change in the isolated area which induces a flow of fluid in the formation (shown in FIG. 1 by flow lines 116).

FIGS. 2a, 2b, 3a, and 3b show embodiments of NMR tool components that may be used in accordance with the principles of the present invention to measure flow velocity, either in conjunction with the NMR tools of FIG. 1, or other NMR tool configurations. The NMR tool components of FIGS. 2a, 2b, 3a, and 3b, as well as the NMR tool components shown in FIG. 4 also include the capability to provide pressure measurements when pressed against the wall of the wellbore (contrary to the device shown in FIG. 1 that is held away from the wellbore wall by packer modules). Moreover, while the fields of the device shown in FIG. 1 are axially symmetric, the fields of the NMR tool components of FIGS. 2a, 2b, 3a, 3b, and 4 are not.

FIGS. 2a and 2b show one embodiment of an NMR tool pad 200 that could be used on NMR tool 108, NMR tool 504 (describe below) or in other NMR tool configurations not shown. Pad 200 includes back-up plate 202, sealing element 204, and pressure monitor probes 206. Additionally, resonance region 208, which is similar to resonance lines 120 of FIG. 1 (but, contrary to resonance lines 120, are not axially symmetric), illustrates the sensitivity to motion along an imaginary line joining the pressure probes 206 (of FIG. 2a). If used with logging device 100, pad 200 would actually be rotated 90° so that resonance region 208 conforms with resonance lines 120. Moreover, in order to utilize pressure monitor probes 206, pad 200 must be configured such that it is placed against the wellbore wall (see, for example, the NMR tool configuration shown in FIG. 5 and the corresponding text below) and hydraulic communication is made between probes 206 and the formation.

FIGS. 3a and 3b show another embodiment of an NMR tool pad 300 that could be used on NMR tool 108, NMR tools 400 and 500 (described below) or on a single NMR tool (not shown) that is configured to produce two different resonance regions (i.e., vertical and horizontal). Pad 300 includes back-up plate 302, sealing element 304, pressure monitor probes 306 that measure pressure azimuthal gradients 316, pressure monitor probes 312 that measure elevational gradients 322 and fluid inlet port 314 that draws fluid into the logging device. Additionally, resonance region 308 illustrates the sensitivity to radial motion, while resonance region 318 illustrates the sensitivity to vertical motion. It should be noted that, because a pressure sensor is not placed into the formation, the radial component of the pressure drop is not measured. Assuming that the formation is isotropic in the horizontal plane, then the radial permeability component is substantially similar to the azimuthal component. Thus, obtaining an azimuthal measurement via probes 306 provides a radial answer.

It should be noted that, in accordance with the principles of the present invention, the shaped resonance regions are not limited simply to cylinders and flattened-toroids, and that the tools described above are merely illustrative of how the present invention may be applied to such devices. For example, the pads of FIGS. 2a and 3a are generally sensitive to motion in the circumferential direction, i.e., rotation of the drill string within the borehole. Thus, the present invention may be utilized to produce specific-shaped resonance regions that are substantially smaller in one direction than any other direction, and that the smaller direction is beneficial because it provides measurements that essentially are unaffected by movement in that direction. For example, the thin, long, cylindrically-shaped region is generally unaffected by vertical movement.

FIG. 4 shows another embodiment of a logging device 400 that may be used in accordance with the principles of the present invention. Rather than utilize a single pad 300 to perform a wide variety of functions (which accordingly increases the complexity and expense of producing such a pad), device 400 offers an alternative when used in conjunction with, for example, pad 200 of FIG. 2a. Device 400 includes pressure monitor probes 402, 404 and 406, another NMR tool (not shown) and a fluid sampling probe 408 that is used to sample formation fluid instead of fluid inlet port 314 of pad 300 (see FIG. 3a).

Device 400 has multiple applications. First, NMR probes 402, 404 and 406 may be utilized to obtain a small-scale permeability measurement (in both vertical and horizontal directions) of the invaded zone, i.e., the zone of the formation affected by drilling damage. Second, probes 406 and 408 may be used to perform a "deeper" permeability measurement by conducting a pressure interference test between the probes (provided the spacing between probes 406 and 408 is sufficiently large). Probe 408 would be used to create a pressure pulse by withdrawing fluid into the probe. A comparison of the two different permeability measurements (i.e., the small-scale or invaded zone measurement, and the "deeper" or virgin reservoir) provides information on the formation heterogeneity. In addition, if the extent of the damaged zone is available, for example, from an array resistivity log, then a value of the "skin" also may be determined.

Persons skilled in the art will appreciate that, although three specific configurations of logging tools have been described, that there are countless other combinations that may be used to practice the principles of the present invention. For example, a fifth probe could be placed opposite probe 402 on device 400. In such a configuration, probes 404, 406 and 408 may be of the type shown in FIG. 3a, while probes 402 and the fifth probe may be of the type shown in FIG. 2a. Device 400 also would have the capability to determine permeability using the pressure interference test while determining small-scale permeability using the NMR techniques described herein.

FIG. 5 shows a schematic illustration of another embodiment of the present invention in which an NMR logging device 500 measures local pressure gradients so that parameters such as permeability and skin damage may be determined. Logging device 500 includes an NMR tool 504 and packers 506 and 508. Packers 506 and 508 operate as described above to create a specific flow path within the earth formation. NMR tool 504 includes pressure sensor 530 and NMR tool pads 534 and 536, each of which may be similar to the NMR tool pads described above. For example, NMR tool pad 534 may be used to form resonance region 518 in the formation surrounding wellbore 510. More importantly, NMR tool 504 also includes moveable springs 532 that press pressure sensor 530 against wellbore wall 511 so that local pressure gradient measurements may be obtained.

To determine the skin damage, probes 534 and 536 determine the small-scale permeability (i.e., local permeability of the damaged zone). Fluid then is flowed into the region between packer modules 506 and 508, which breaks the mudcake seal, to induce a large pressure pulse. The pressure pulse is used to perform an interference test between the packer probe and another probe (not shown) located outside the packer region. Persons skilled in the art will appreciate that the small-scale NMR permeability measurement must be made prior to breaking the mudcake seal and the interference test when utilizing device 500. Moreover, with the addition of a pressure gauge (not shown) located between packer modules 506 and 508, device 500 also may be utilized for the determination of skin and formation pressure.

When formation pressure is being determined, packer modules 506 and 508 are utilized to isolate a portion of the wellbore. NMR probe 504 is utilized to produce resonance shell 518 that is used to sense when there is no mud filtrate invasion into the formation—that filtrate fluid speed is zero. Pressure monitor probe 530 senses the pressure on the other side of the mudcake from the wellbore, while another pressure sensor (not shown) located between the packers monitors the pressure in the packer interval. Fluid is then withdrawn or injected until a zero fluid speed condition exists, at which point the pressure in the packer interval should be the same as the formation pressure.

The methods of quantitative interpretation are simplified when a uniform gradient field is present because in a uniform gradient $\hat{G}$, the relationship between a displacement vector $\hat{r}(t)$ and a change in resonance frequency $\delta\omega$ also is a function of one parameter: $\hat{G} \cdot \hat{r} = \delta\omega$. Therefore, every change in resonance frequency corresponds to a particular displacement and $\delta\omega_i$ at the time $I^*t_e$ of echo I can be related to an average velocity $r/(I^*t_e)$. Every echo I of a given echo train thus represents an experiment with a different "mixing" time $(I^*t_e)$ in the sense of the standard NMR exchange experiments. However, the signal-to-noise ratio can be enhanced by using all of the echoes together to extract velocity. For example, an analysis of the echo shape f(t) (or echo spectrum f(ω)) only provides information regarding where the sum of the spins moved, but does so in a fast and efficient manner so that few NMR experiments are needed. If more information is required, such as a determination of where each spin is moving, frequency selective experiments (either one-dimensional or two-dimensional) may be performed, but such experiments are more demanding in terms of measurement time and the number of measurements required. As a variation from the previously described NMR techniques, this embodiment of the present invention requires that the spins be marked or labeled in dependence of their resonance frequency by applying RF pulses either immediately before or after the excitation pulse. The simplest way of marking would be a saturation sequence that creates a resonance frequency dependent saturation pattern. A measurement of velocity may then be obtained by correlating resonance frequency at two different times.

Figure 6A:
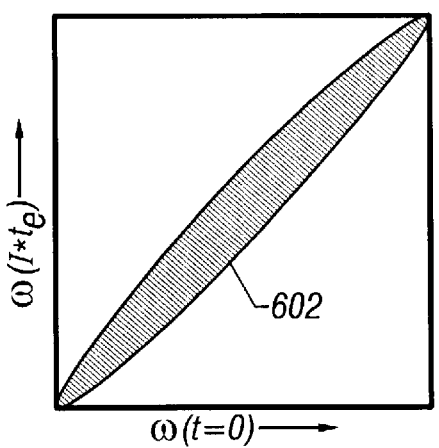
FIGS. 6a–e are schematic examples of acquired exchange distribution and the effects of frequency displacement for a given echo in accordance with the present invention.
Figure 6B:
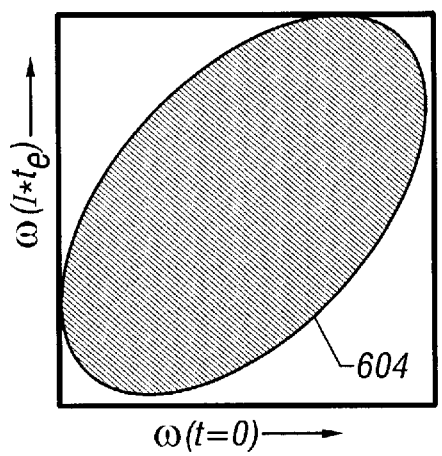
Figure 6C:
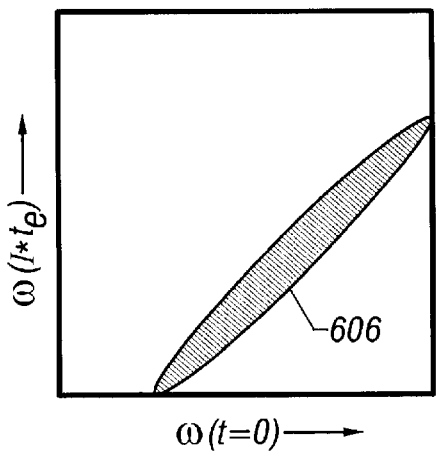
Figure 6D:
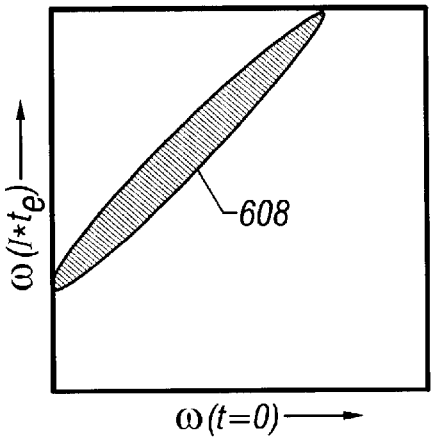
Figure 6E:
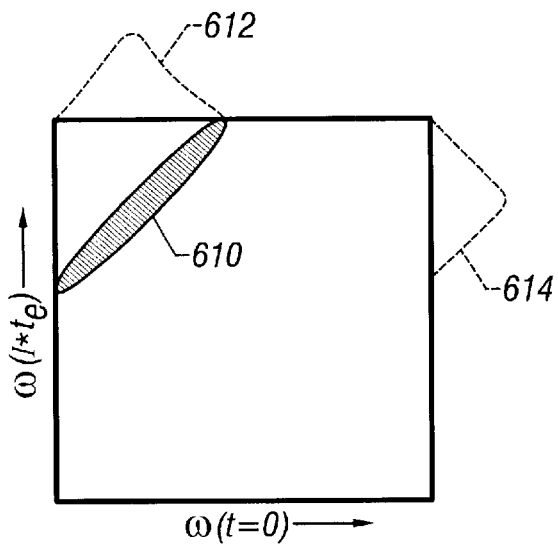

FIGS. 6a–6e show various schematic examples of two-dimensional exchange spectra of the I-th echo. FIG. 6a shows a two-dimensional distribution 602 for the I-th echo in the absence of displacement and translational diffusion. FIG. 6b shows a two-dimensional distribution 604 for the I-th echo that indicates the influence of strong diffusion (or statistical displacement). FIG. 6c shows a two-dimensional distribution 606 that is the result of displacement occurring in the lower field with a given velocity v. FIG. 6d shows a similar two-dimensional distribution 608 that results from motion having the same velocity, but opposite direction (i.e., into the high field). Finally, FIG. 6e shows the result of doubling the velocity shown in FIG. 6d (the result would be the same whether velocity (v), "mixing" time $(I^*t_e)$ or echo number $(2^*I)$ were doubled). FIGS. 6a–6e show that, in this embodiment, only frequency displacement affects the determination of flow velocity (versus decay amplitude as described above). Persons skilled in the art will appreciate that the data shown in FIGS. 6a–6e, without encoding (i.e., just measuring echo shape) would appear as curved projections instead of spectra, as shown by way of illustration in FIG. 6e by dashed line curves 612 and 614. Similar projections also could be produced for each of FIGS. 6a–6d, if desired.

Figure 7:
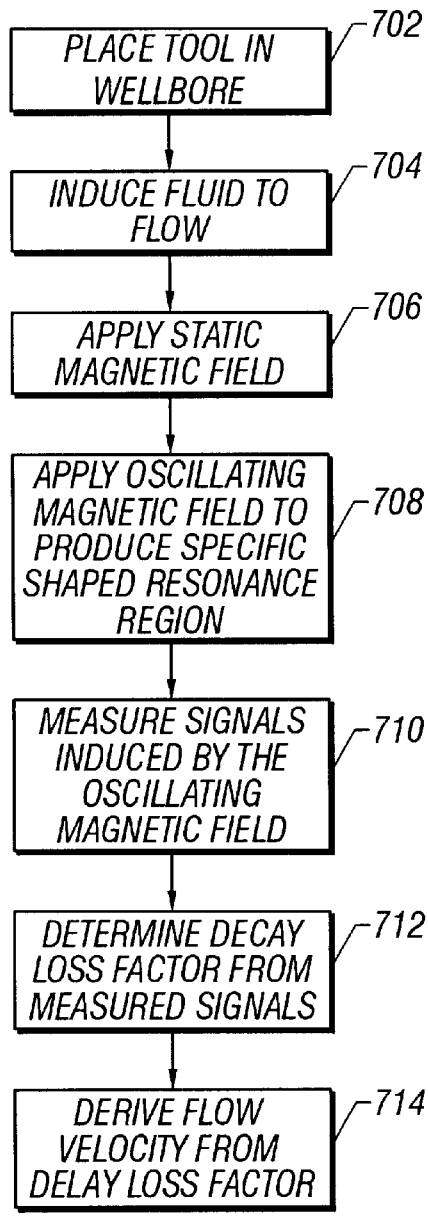
FIG. 7 is a flow chart illustrating steps for determining flow velocity in accordance with the principles of the present invention.

FIG. 7 shows a flow diagram that illustrates the methods of the present invention for determining flow velocity. In a step 702, the tool is placed in the wellbore (depending on exactly which tool and the desired parameters, step 702 may be performed as part of drilling operations or it may be performed separate from drilling operations, for example, when local gradient pressure measurements are necessary). Fluid is induced to flow in a step 704 in any known manner. For example, via external pumping using equipment from the top of the borehole or by utilizing pumping ports on the well logging tool itself, as shown in FIG. 3a (i.e., fluid inlet port 314).

A strong, polarizing, static magnetic field is applied to the formation in a step 706, through the use of, for example, permanent magnets, that polarizes a portion of the formation (i.e., longitudinal magnetization). An oscillating magnetic field then is applied in a step 708 in accordance with field maps $B_0$ and $B_1$, to produce a resonance region having a specific shape dictated by the desired motion sensitivity. The oscillating magnetic field is the result of the application of a series of RF pulses to the formation which forms a resonance region. The specific shape of the resonance region, which is determined by the specific sequence of RF signals, is chosen depending on the desired axis of sensitivity. For example, a thin, long, cylindrically-shaped resonance region may be produced for measurements that require minimal impact by vertical displacement of the drill string.

The sequence of applied RF pulses excites specific nuclear spins in the formation that induce a series of spin echoes. The spin echoes induced by the oscillating magnetic field are measured in a step 710. The decay loss factor is determined in a step 712 (e.g., if there is no movement, the decay loss factor will be unity). Finally, the flow velocity is derived, in a step 714, from the decay loss factor. Persons skilled in the art will appreciate that other parameters, such as permeability, require additional steps not shown in FIG. 7 (for example, in order to determine permeability, a step of measuring local pressure gradients must be added).

One advantage of the change in resonance frequency measurement of flow velocity is that, for identical conditions, the resonance frequency measurement provides detection of much smaller displacement velocities compared to the decay amplitude embodiment previously described. However, the frequency selective analyses (both one-dimensional and two-dimensional) require the presence of a uniform gradient field that is not a requirement of the echo shape and decay analysis. Thus, under circumstances where a uniform gradient exists and very thick resonance regions are required, resonance frequency measurements may be particularly advantageous. Moreover, the spread in displacement could be analyzed in terms of free fluid, bound fluid, viscosity or the interaction of the fluid with the rock surface to provide additional information about the formation and the fluids present therein.

Many of the previously described NMR measurements of flow velocity rely on a relatively high gradient in $B_0$. Therefore, those measurement techniques are not useful under circumstances where saddle-point measurements need to be made. A saddle-point tool can be used to measure flow velocity, however, a gradient in the pulse amplitude $B_1$ is present. There are various known techniques for applying magnetic field gradients to produce stimulated echoes, however, those techniques all require an inhomogeneous $B_1$ encoding pulse followed by the application of a homogeneous $B_1$ refocusing pulse and homogeneous $B_1$ reading pulses. Inside out NMR saddle-point tools naturally produce the required strongly inhomogeneous $B_1$ field (from the RF coil), but the substantially homogeneous $B_1$ field simply is not achievable.

Figure 8:
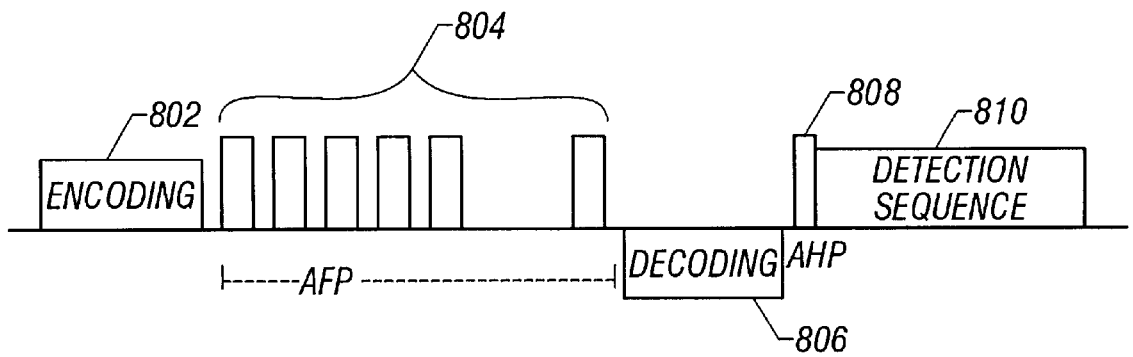
FIG. 8 is a pulse sequence illustrating the use of adiabatic pulse echoes in accordance with the present invention.

The refocusing/reading pulse may, in accordance with the present invention, be accomplished with the inhomogeneous $B_1$ field by utilizing adiabatic methods as shown in FIG. 8. For example, following encoding pulse 802 (that spirals the spins between the longitudinal and a transverse direction), a series of adiabatic refocusing pulses (AFP) 804 are applied to create an echo train. The echo train is then spooled back by applying a negative encoding pulse 806 to decode the echo train. Then, excitation may be performed adiabatically by applying an adiabatic fast half passage pulse (AHP) 808 into the resonance zone just prior to the application of detection sequence 810.

Detection sequence 810 may be accomplished by applying an adiabatic fast half passage pulse into the resonance zone starting at a frequency outside of the resonance zone, varying the frequency of the refocusing pulse so that it sweeps through the entire resonance zone, and stopping at the resonance frequency. Alternately, the $B_0$ field may be varied instead of the frequency. In addition, if diffusion is present, its effects may be suppressed by applying a multi-echo sequence with many refocusing pulses, such as refocusing pulse sequence 804, to introduce phase errors that cancel themselves out when an even number of refocusing pulses are applied. For the detection sequence, a single echo or a multi-echo train may be utilized. Effective excitation may be provided by an adiabatic pulse by applying an adiabatic half passage pulse to turn the spins into the transverse plane.

The capability to measure flow velocity provides additional advantages. For example, NMR apparatus may be installed within a drill string and operated during a pause in drilling operations to provide immediate feedback. One particularly useful parameter that may be determined is a direct measurement of permeability based on Darcy's formula which states:

$$v = \frac{1}{\mu} K * grad * p \qquad (3)$$

where v represents seepage velocity, $\mu$ represents fluid viscosity, K represents the permeability (tensor) and p is the local value of the fluid pressure. In earth formations at the scale of the measurements addressed herein, the permeability K is essentially determined by two independent values $K_h$ and $K_v$ (i.e., the horizontal component and the vertical component, respectively).

By applying the NMR measurements described above to determine local fluid velocity, values for $K_h$ and $K_v$ may be directly obtained (provided that probes are set to measure local pressure gradients, such as the configurations shown in FIGS. 4 and 5). For example, $K_v = \mu v_z / dp/dz$. Assuming the fluid viscosity $\mu$ is known, dp/dz easily may be obtained through the use of pressure monitor probes, and because $v_z$ is determined based on one of the above-described NMR measurements, $K_v$ can be determined. If it is assumed that the permeability is isotropic in the transverse plane, then an azimuthal measurement of the pressure gradient utilizing pressure monitor probes and a measurement of fluid velocity (as described above) provides Kh (based on the derivation that $K_h = \mu v_\theta r_w / dp/d\theta$). Once $K_h$ and $K_v$ are determined, permeability K is also determined, in this case in situ. However, it should be noted that, as described above, because local pressure gradient measurements can not be obtained during drilling operations (because the sensor probes must be placed against the wellbore wall), neither can permeability measurements be made during drilling operations.

Another parameter that may be determined using the flow velocity measurements of the present invention is an assessment of drilling damage (i.e., the alteration of permeability into the formation a radial distance $r_d$ due to drilling operations). This assessment may be determined by determining the additional pressure drop or "skin" S associated with the altered region of the formation when fluid flows into the wellbore (as this assessment also relies on a measurement of local pressure gradient, it also cannot be performed during drilling operations). The determination of S is based, at least in part on the permeabilities of the virgin formation and the damaged formation. Thus, skin S may be calculated as follows:

$$S = \left(\frac{K_\infty}{K_d} - 1\right) \ln\left(\frac{r_d}{r_w}\right) \qquad (4)$$

where $r_w$ is the wellbore radius, and $K_\infty$ and $K_d$ are the permeabilities of the virgin formation and damaged zones, respectively. Accordingly, once $r_d$ is determined from for example, array resistivity logs, a detailed, depth-resolved model of the damaged zone can be constructed and a value of the skin may be determined.

It is also possible to take measurements of formation pressure, however, such measurements, as explained above, also cannot be taken while drilling is active. Formation pressure may be measured by applying the velocity measurement principles described above, and detecting the condition when the formation fluid is at rest (i.e., motionless). This may be accomplished by manipulating the wellbore pressure while monitoring the measured velocity. When the measured velocity is zero, the local pressure at the test depth must be equal to that of the formation (such that no fluid flows either from the wellbore into the formation (i.e., invasion), or vice versa). At that instant, the mud pressure, which can be determined using conventional tools, is an accurate measure of the formation pressure.

It should be recognized that it may be difficult to determine the zero velocity condition, because resolution decreases at low velocities. In that case, formation velocity could be measured while adjusting wellbore pressure in discrete steps. A plot of the measured velocity as a function of local wellbore pressure may be extrapolated to determine the pressure at which zero velocity would occur. While nonlinearities in the mudcake transmissivity may be manifested in the pressure-velocity relationship, such steps may be necessary where it is prohibitive to reduce the well pressure well below formation pressure.

When, for reasons of well control, safety or precision in measurement, it is desirable to adjust the pressure in the entire wellbore, the local formation pressure may be determined by the application of principles shown in FIG. 5, as described above. An NMR experiment to measure formation pressure could be conducted using a three module logging device where a radially sensitive NMR tool is located between two packer modules (as shown by modules 504, 506 and 508). The packer modules 506 and 508 could isolate a portion of the wellbore 510 and NMR module 504 could include a pumpout unit that would inject and/or extract fluid into/from the isolated interval in order to adjust the pressure in the isolated portion of the wellbore. A conventional pressure probe 530 also could be utilized within the packer interval that directly measures the pressure of the sandface interface (i.e., the interface between the mudcake and the formation) in order to accurately determine the transmissivity of the mudcake. Such techniques may not be suitable for low permeability formations where steady pressure conditions may not be achievable in the time period allocated for testing.

The development of the mudcake itself is another important parameter that may be determined in accordance with the NMR measurements of velocity described above. It is important to be able to determine the rate of loss of mud filtrate into the formation (i.e., invasion), which is an accurate indicator of the overall quality of the mud system being employed. Mud filtration rate may be determined by integrating fluid flow measurements over a cylindrical surface concentric with the wellbore. The result is a direct measurement of the volumetric flux of the invading fluid provided that near steady-state conditions are present (for example, the rate at which mud filtrate invades the formation should be substantially constant). Thus, this parameter also cannot be determined while drilling is occurring.

We claim:

1. A method of determining flow velocity of a fluid in an earth formation utilizing at least one nuclear magnetic resonance (NMR) tool that is placed in a wellbore in the formation and which produces a static magnetic field and measures induced magnetic signals, the method comprising:
   inducing the fluid to flow;
   applying the static magnetic field from the NMR tool to a volume of the formation, the static magnetic field polarizing a substantial portion of the formation that is subject to the static magnetic field;
   applying an inhomogeneous oscillating magnetic field to a specific region of the polarized portion via an encoding pulse to mark spins in the specific region;
   reapplying the inhomogeneous oscillating magnetic field to the specific region via an even number of refocusing pulses that induce the production of measurable signals in the specific region;
   measuring amplitude of the induced signals; and
   deriving the flow velocity based on the measured amplitude.

2. The method of claim 1, wherein the inhomogeneous oscillating magnetic field is applied in accordance with field maps $B_0$ and $B_1$ to produce a long cylindrically shell-shaped resonance region in the formation and the determination of flow velocity is sensitive to radial flow.

3. The method of claim 1, wherein the inhomogeneous oscillating magnetic field is applied in accordance with field maps $B_0$ and $B_1$ to produce a flattened torus-shaped resonance region in the formation and the determination of flow velocity is sensitive to vertical flow.

4. The method of claim 1, wherein the inhomogeneous oscillating magnetic field is applied in accordance with field maps $B_0$ and $B_1$ to produce a shaped resonance region in the formation and the determination of flow velocity is sensitive to circumferential flow.

5. The method of claim 1, wherein the inhomogeneous oscillating magnetic field is applied in accordance with field maps $B_0$ and $B_1$ to produce a saddle-point-shaped resonance region in the formation.

6. The method of claim 1, wherein applying the inhomogeneous oscillating magnetic field comprises:
   applying, via a first NMR tool, a first. encoding pulse in accordance with specific field maps $B_0$ and $B_1$ to produce a resonance region having a long cylindrical shell-shape to establish rotation in spins located in a first part of the specific region and to induce the production of measurable signals that are sensitive to radial flow; and
   applying, via a second NMR tool, a second encoding pulse in accordance with specific field maps $B_0$ and $B_1$ to produce a resonance region having a flattened torus-shape to establish rotation in spins located in a second part of the specific region and to induce the production of measurable signals that are sensitive to vertical flow.

7. The method of claim 6, wherein reapplying the inhomogeneous oscillating magnetic field comprises:
   reapplying, via a first NMR tool, at least a first even number of refocusing pulses having the same inhomogeneous oscillating magnetic field as the first adiabatic encoding pulse to the first part of the specific region; and
   reapplying, via a second NMR tool, at least a second even number of refocusing pulses having the same inhomogeneous oscillating magnetic field as the second adiabatic encoding pulse to the second part of the specific region.

8. The method of claim 7, wherein the first and second NMR tools are included within a drill string and NMR measurements of flow velocity are made while drilling of the wellbore occurs.

9. The method of claim 7, further comprising:
   taking a local pressure gradient measurement;
   deriving a horizontal component of flow velocity from the measurable signals induced by the first NMR tool;
   deriving a vertical component of flow velocity from the measurable signals induced by the second NMR tool; and deriving a measurement of permeability from the horizontal component, the vertical component and the local pressure gradient measurement.

10. The method of claim 1, wherein the NMR tool is included within a drill string and NMR measurements of flow velocity are made while drilling of the wellbore occurs.

11. The method of claim 1, wherein the induced signals are echoes and measuring amplitude of the induced signals comprises:

detecting a single echo.

12. The method of claim 1, wherein the induced signals are echoes and measuring amplitude of the induced signals comprises:

detecting a multi-echo train.

13. The method of claim 1, wherein the specific region has a resonance region and reapplying the inhomogeneous oscillating magnetic field comprises:

applying an adiabatic fast full passage pulse through the resonance region by varying the frequency of the refocusing pulses so that the pulses are applied prior to one end of the region, through the region, and up to resonance frequency.

14. The method of claim 1, wherein the specific region has a resonance region and applying the inhomogeneous oscillating magnetic field comprises:

applying an adiabatic fast half passage pulse into the resonance region by varying the frequency of the adiabatic pulses so that the pulses are applied prior to one end of the region and into the region.

15. The method of claim 1, wherein the even number of refocusing pulses comprise a plurality of refocusing pulses that suppress decay due to translational diffusion so that amplitude measurements are dependent mainly on velocity only when diffusion is present.

16. The method of claim 1, further comprising distinguishing diffusion from induced fluid flow.

* * * * *